United States Patent [19]

Borzatta et al.

[11] 4,378,373

[45] Mar. 29, 1983

[54] DERIVATIVES OF BENZOYLPHENOXYALKANOIC ACIDS HAVING NORMOLIPEMIZING ACTIVITY

[75] Inventors: Valerio Borzatta; Manlio Cristofori; Mauro Morotti, all of Bologna; Giuseppe Mascellani, Calderino di M.S. Pietro, all of Italy

[73] Assignee: Alfa Farmaceutici S.p.A., Italy

[21] Appl. No.: 255,430

[22] Filed: Apr. 20, 1981

Related U.S. Application Data

[60] Division of Ser. No. 123,454, Feb. 21, 1980, Pat. No. 4,296,125, which is a continuation of Ser. No. 29,006, Apr. 11, 1979, abandoned.

[30] Foreign Application Priority Data

May 9, 1978 [IT] Italy .................................. 3426 A/78
Dec. 21, 1978 [IT] Italy .................................. 3630 A/78

[51] Int. Cl.[3] .................. A61K 31/24; A61K 31/195; C07C 00/00
[52] U.S. Cl. ...................................... 424/309; 560/15; 560/30; 562/441; 562/426; 424/319
[58] Field of Search ................. 562/441, 426; 560/30, 560/15; 424/309, 319

[56] References Cited

U.S. PATENT DOCUMENTS

| | | | |
|---|---|---|---|
| 3,828,093 | 8/1974 | Boys et al. | 562/441 |
| 4,235,896 | 11/1980 | Mieville | 562/441 |
| 4,250,192 | 2/1981 | Sallmann et al. | 424/309 |
| 4,277,497 | 7/1981 | Fromantin | 424/317 |
| 4,323,691 | 4/1982 | Ours et al. | 562/441 |

FOREIGN PATENT DOCUMENTS 2948095 6/1981 Fed. Rep. of Germany ........ 560/36

*Primary Examiner*—James H. Reamer
*Attorney, Agent, or Firm*—Stevens, Davis, Miller & Mosher

[57] ABSTRACT

Derivatives of benzoylphenoxyalkanoic acids corresponding to the formula:

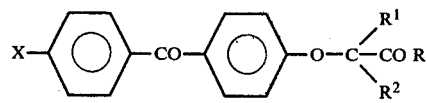

wherein: X represents for example a halogen, $R^1$ and $R^2$ represent for example alkyl groups, R represents for example an aminoacid; and the salts thereof are new products showing antilipaemic and anticholesterolemic pharmacological activity.

12 Claims, No Drawings

4,378,373

DERIVATIVES OF BENZOYLPHENOXYALKANOIC ACIDS HAVING NORMOLIPEMIZING ACTIVITY

This is a division of application Ser. No. 123,454 filed Feb. 21, 1980, now U.S. Pat. No. 4,296,125 which in turn is a continuation of application Ser. No. 29,006 filed Apr. 11, 1979, now abandoned.

FIELD OF THE INVENTION

The present invention relates to products which are active in reducing the triglyceride and cholesterol content in the blood and therefore are suitable to be used in the therapy of hyperlipaemia and of hypercholesterolemia, which are considered the main causes of some coronary diseases and of atherosclerosis.

SUMMARY OF THE INVENTION

The subjects of the present invention are new products, derivatives of benzoylphenoxyalkanoic acids, having antilipaemic and anticholesterolemic pharmacological activity, corresponding to the following formula:

$$X-\text{C}_6\text{H}_4-CO-\text{C}_6\text{H}_4-O-C(R^1)(R^2)-COR$$

wherein:
   X represents an atom of chlorine, bromine, iodine or an alkyl group having 1 to 4 carbon atoms;
   $R^1$ and $R^2$, equal or different from each other, represent a hydrogen atom or an alkyl group or a hydroxyalkyl group, said groups having 1 to 6 carbon atoms;
   R represents a group selected from:

$$-N(R^3)-C(R^4)(R^5)-COZ$$

wherein: $R^3$ represents a hydrogen atom or an alkyl group, $R^4$ and $R^5$, equal or different from each other, represent a hydrogen atom or an alkyl, an hydroxyalkyl, mercaptoalkyl, alkylaryl, aryl group, wherein the alkyl groups have up to 6 carbon atoms and the aryl groups may have substituents and Z represents an OH or alkoxy group having 1 to 6 carbon atoms,

NH—CH$_2$CONH—CH$_2$COOH

NH—CH$_2$—CH$_2$—OCO—(pyridyl)

NH—CH$_2$—CH$_2$—CH$_2$—OCO—(pyridyl)

NH—CH$_2$—CH$_2$—SO$_3$H

O—CH$_2$—CH$_2$—S—CH$_2$—CH$_2$—O—

O—CH$_2$—COZ wherein Z has the abovementioned meaning

NH—N(piperidinyl/homopiperidinyl) (CH$_2$)$_n$ wherein n is equal to 5 or 6 an oxydrile an alkoxy group having 1 to 6 carbon atoms

O—CH$_2$CH$_2$—OCO—(pyridyl)

O—CH$_2$CH$_2$CH$_2$—OCO—(pyridyl)

O—CH$_2$CH$_2$—NH—CO—(pyridyl)

N(CH$_2$CH$_2$—OA)(CH$_2$CH$_2$—OA)

wherein the two A groups, equal or different from each other, are selected from:

Cl—C$_6$H$_4$—O—C(CH$_3$)$_2$—CO—

(pyridyl-3)-CO—

(3,4,5-trimethoxyphenyl)-CO— or hydrogen
R being furthermore selected from the divalent radicals:

N(CH$_3$)(OCH$_2$CH$_2$)(OCH$_2$CH$_2$)

N(A)(OCH$_2$—CH$_2$)(OCH$_2$—CH$_2$)

wherein A has the abovementioned meaning; and pharmacologically acceptable salts of said derivatives.

It is evident that when R represents a divalent radical, the two valencies of the latter are intended as saturated by two radicals of substituted benzoylphenoxyalkanoic acids.

Further subjects of the present invention are the pharmacologically acceptable salts that the hereinbefore defined derivatives, containing acid groups in their molecule, may form with non-toxic cations, as for example sodium, potassium, magnesium, etc., and with non-toxic amines, as for example dicyclohexylamine, dibenzylethylenediamine, etc.

Further subjects of the present invention are the pharmacologically acceptable salts that the hereinbefore defined derivatives, containing basic groups in their molecule, may form with non-toxic anions.

Examples of said salts are: chlorhydrates, bromhydrates, sulfates, nitrates, acetates, propionates, succinates, adipates, glycolates, lactates, malates, ascorbates, piruvates, tartrates, maleates, citrates, bicarbonates, pamoates, phenylacetates, benzoates, salicylates, alkylsulfates, arylsulfates, glucuronates, salts with methionine, lysine and arginine.

DETAILED DESCRIPTION

The processes used for preparing the products of this invention consist in reacting the halogenide of 2-(4-(4-substituted-benzoyl)phenoxy)-2-alkyl-alkanoic acid with the proper amine and with the proper compound containing the alkyl oxydrile, in the presence of inert solvents and of an agent suitable for neutralizing the halogenidric acid which is formed by the condensation.

In the case of products containing simultaneously ester groups and amide groups, the esterification reaction is generally carried out on the amide. In some cases it is possible to invert the order of the reaction, that is to carry out the reaction which forms the amide on the compounds which already contain the ester groups.

The products containing free carboxyl groups may be prepared from the corresponding alkyl esters by means of an alkaline hydrolysis.

The products of this invention possess a valuable pharmacological activity, which makes them suitable to be used as antilipaemic and anticholesterolemic drugs.

The products of this invention may be administered in the form of pharmaceutical preparations containing an effective dose of such products in combination or in admixture with excipients suitable for oral or parenteral administration.

Tablets and capsules are preferred, which in addition to the active ingredient contain: (a) diluents, e.g. lactose, dextrose, sucrose, mannitol, sorbitol, cellulose and/or glycerol; (b) lubrificants, e.g. silica, talcum, stearic acid, its magnesium or calcium salts and/or polyethylenglycols; and for the tablets (c) binding agents, e.g. aluminum and magnesium silicates, starch, gelatine, tragacanth, methylcellulose, sodium carboxymethylcellulose and/or polyvinylpyrrolidone; and occasionally (d) disgregating agents, e.g. starch, agar, alginic acid or its sodium salts, enzymes effective on the binding agents, effervescent mixtures and/or (e) adsorbents, dyes, flavours and sweeteners.

Injectable compositions are preferably aqueous solutions or isotonic suspensions.

The pharmaceutical compositions may be sterilized and/or may contain adjuvants, such as preservatives, stabilizers, wetting agents or emulsifiers, solution promoters, salts to regulate the osmotic pressure and/or buffers.

Said pharmaceutical preparations may contain, additionally, other substances having pharmacological activity.

The above pharmaceutical preparations are prepared according to conventional methods.

The following examples are supplied with the purpose of illustrating this invention without limiting in any way the scope thereof.

The I.R. spectra of the examples have been carried in KBr; the maximum absorption frequency ($cm^{-1}$) of the I.R. spectra is provided.

The elemental analysis of all the products prepared in the examples was in agreement with the expected formulae.

EXAMPLE 1

(2-(4-(4-chlorobenzoyl)phenoxy)-2-methyl-propanoyl) aminoacetic acid

A solution of 6.76 g (20 millimoles) of 2-(4-chlorobenzoil)phenoxy)-2-methyl-propanoyl chloride in 30 ml of ethylic ether and 10 ml of 2 N NaOH aqueous solution were added slowly at cool to a solution of 1.84 g (20 millimoles) of 2-aminoacetic acid in 20 ml of water. After stirring for 3 hours at cool and for 8 hours at room temperature, the aqueous phase was separated, washed with ethylic ether, brought to pH 3–3.5 by means of hydrogen chloride and extracted with ethylic ether. The extracted, washed twice with water and dried, was evaporated under vacuum. The residual oil was fractionally crystallized from n-buthyl bromide, thus obtaining 3.3 g of product (m.p. 144°–146° C.) with a yield of 43.9%.

I.R. Spectrum: 3380, 3280, 3040, 2970, 2920, 1730, 1655, 1595, 1520, 1500, 1410, 1395, 1300, 1280, 1270, 1235, 1145, 1085, 1015, 955, 925, 850, 835, 765, 675.

EXAMPLE 2

(2-(4-(4-chlorobenzoyl)-phenoxy)-2-methyl-propanoyl-)amino acetyl)aminoacetic acid A solution of 3.38 (10 millimoles) of 2-(4-(4-chlorobenzoyl)phenoxy)-2-methyl propanoyl chloride in 25 ml of ethylic ether and 10 ml of 1 N NaOH aqueous solution were contemporaneously added, at cool and under stirring, to a solution of 1.32 g (10 millimoles) of N-(aminoacetyl)aminoacetic acid in 10 ml of 1 N aqueous solution of sodium hydroxide. After stirring for 3 hours at cool and for 8 hours at room temperature, the aqueous phase was separated and washed twice with ethylic ether. The pH was brought to 3–3.5. The separated orange yellow oil was washed with ethylic ether, was dissolved in methanol and the solution was dried. After evaporation under vacuum, the residual was crystallized from isobuthanol, thus obtaining 1.45 g of product (m.p. 102°–103° C.) with a yield of 33.5%.

I.R. Spectrum: 3460, 3390, 3050, 2970, 2920, 1725, 1650, 1590, 1520, 1500, 1490, 1405, 1390, 1380, 1310, 1300, 1280, 1270, 1235, 1145, 1085, 1010, 955, 925, 850, 835, 760.

EXAMPLE 3

2(4-(4-chlorobenzoyl)phenoxy)-2-methyl-propanoyl)-amino ethyl nicotinate

A solution of 3.38 g (10 millimoles) of 2-(4-(4-chlorobenzoyl)phenoxy)-2-methyl-propanoyl chloride in 15 ml of pyridine was added at cool to a solution of 2.38 added at cool to a solution of 2.38 g (10 millimoles)

of nicotinate of 2 amino ethanol chloridrate in 30 ml of pirydine. After stirring for 2 hours at cool and for 10 hours at room temperature, the obtained salt was filtered and evaporated under vacuum. The residual was dissolved in 30 ml of methylene chloride, washed with 30 ml of a NaOH aqueous solution (10%) and then twice with water. The organic phase was dried and evaporated, and the residual was crystallized from a mixture benzene/petroleum ether (4060°) 1/1 (v/v), thus obtaining 2.8 g of product (m.p. 134°–135°) with a yield of 63.8%.

I.R. spectrum: 3210, 3060, 3040, 2980, 2920, 1720, 1650, 1590, 1465, 1415, 1385, 1365, 1300, 1280, 1240, 1205, 1190, 1145, 1085, 970, 925, 855, 765, 750, 700.

EXAMPLE 4

N-(2-(4-(4-chlorobenzoyl)phenoxy)-2-methyl-propanoyl)diethanolamine

A solution of 3.36 g (10 millimoles) of 2-(4-(4-chlorobenzoyl)phenoxy)-2-methylpropionyl chloride in 15 ml of acetone were added, slowly under stirring at room temperature, to a solution of 2.1 g (20 millimoles) of diethanolamine in 30 ml of acetone.

After stirring for 5 hours at room temperature, filtering and evaporation of the solvent, the residual was dissolved in methylene chloride, washed once with hydrogen chloride and twice with water. The organic phase was dried, evaporated under vacuum and the residual oil was crystallized from benzene, thus obtaining 3.1 g of product (m.p. 128°–129° C.) with a yield of 76.5%.

I.R. spectrum: 3420, 3020, 2980, 2920, 2870, 1640 (wide), 1595, 1500, 1465, 1440, 1410, 1395, 1385, 1365, 1300, 1280, 1240, 1180, 1170, 1145, 1075, 1050, 1010, 950, 930, 860, 845, 765, 680.

EXAMPLE 5

Bis-nicotinate of (2-(4-(4-chlorobenzoyl) phenoxy)-2-methyl propanoyl) diethanolamine dichlorhydrate 1.32 g (6.92 millimoles) of nicotinoyl chloride chlorydrate were slowly added to a solution containing 1.4 g (3.46 millimoles) of N-(2-(4-(4-chlorobenzoyl)-phenoxy)-2-methylpropanoyl) diethylamine and 3 ml of triethylamine in 20 ml of warm benzene. After heating under reflux for 30 minutes and subsequent cooling, further 0.132 g of nicotinoyl chloride chlorhydrate were added.

After heating under reflux for 15 minutes and subsequent cooling, the precipitate was filtered, washed twice with a 1 N NaOH aqueous solution and twice with water. The organic phase was dried and evaporated under vacuum, thus obtaining an oil. The dichlorhydrate of this oil was precipitated by treating the ethereal solution with gaseous hydrogen chloride, thus obtaining 1.5 g of a very hygroscopic product (m.p. 113°–115° C.) with a yield of 63.3%.

I.R. spectrum: 3040, 2980, 2960, 2870, 1715, 1630 (wide), 1590, 1575, 1500, 1465, 1420, 1380, 1365, 1270 (wide), 1230, 1190, 1110 (wide), 1020, 1010, 955, 975, 850, 835, 740 (wide), 700, 660.

EXAMPLE 6

N-(2-(4-(4-chlorobenzoyl)-phenoxy)-2-methyl propanoyl) diethanolamine bis [2-(4-chlorophenoxy)-2-methyl propanoate]

A solution of 1.948 g (5.8 millimoles) of 2-(4-(4-chlorobenzoyl)-phenoxy)-2-methyl propanoyl chloride in 10 ml of methylic ether was slowly added to a solution containing ether was slowly added to a solution containing 2.9 g (5.8 millimoles) of amino diethyl bis-2-(4-chlorophenoxy)-2-methylpropanoate (prepared according to French patent 2085634) and 0.83 ml (6 millimoles) of triethylamine in 30 ml of ethylic ether kept at 0° C.

After stirring for 2 hours at cool and for 2 hours at room temperature, the precipitate was filtered, washed twice with 1 N NaOH aqueous solution, twice with hydrogen chloride and finally twice with water. After drying and evaporation, an oil was obtained which crystallizes from acetone/water (3.5/1). The residual was crystallized from ethanol, thus obtaining 3.1 g of product (m.p. 97°–99° C.) with a yield of 54.3%.

I.R. spectrum: 3040, 2980, 2920, 2860, 1730, 1640 (wide), 1590, 1485, 1465, 1420, 1380, 1370, 1320, 1300, 1280, 1240, 1170, 1140, 1090, 1040, 1010, 960, 930, 850, 825, 765, 670.

EXAMPLE 7

Methylic ester of N-2-(4-(4-chlorobenzoyl)-phenoxy)-2-methyl propanoyl aminoacetic acid 5.1 g of 2-(4-(4-chlorobenzoyl)-phenoxy)-2-methyl propanoyl chloride were added at 0° C. to 1.8 g (15 millimoles) of the chlorhydrate of the methylic ester of 2-amino acetic acid in 50 ml of pyridine. After stirring for 2 hours at cool and for 12 hours at room temperature, and after evaporation under vacuum the residual was treated with 1 N NaOH aqueous solution and with methylene chloride. The organic phase was washed twice with a 3% NaHCO$_3$ aqueous solution, dried and evaporated. The residual oil was crystallized from n-esane, thus obtaining 4.3 g of product (m.p. 112°–114° C.) with a yield 72.9%.

I.R. spectrum: 3280, 3020, 2950, 2920, 1760, 1690, 1650, 1600, 1550, 1450, 1420, 1410, 1330, 1320, 1310, 1270, 1230, 1170, 1115, 1060, 1040, 990, 960, 870, 840, 800, 705, 625.

EXAMPLE 8

N[2-(4-(4-chlorobenzoyl)-phenoxy)-2-methyl propanoyl]amino ethansulfonic

A solution of 2.5 g (20 millimoles) of 2-amino ethansulfonic acid in 20 ml of 2 N NaOH aqueous solution, pre-cooled to 1°–5° C. was added dropwise to a solution of 6.72 g (20 millimoles) of 2-(4-(4-chlorobenzoyl)-phenoxy)-2methyl propanoyl chloride in 40 ml of ethylic ether. After stirring for 1 hour at cool and for 12 hours at room temperature, the aqueous phase was separated, washed twice with ethylic ether, acidified with a 2 N HCl aqueous solution to pH 1 and washed again twice with ethylic ether. The aqueous phase was evaporated under vacuum and the residual was dissolved in 15 ml of methanol, filtered, evaporated under vacuum and the residual oil was dissolved in the heat in benzene, filtered and cooled, thus obtaining 5.9 g of microcrystalline product (m.p. 133°–135° C.) with a yield of 62.1%.

I.R. spectrum: 3260, 3080, 3060, 2990, 2940, 1650, 1615, 1590, 1550, 1495, 1445, 1435, 1415, 1395, 1370, 1310, 1300, 1285, 1275, 1255, 1235, 1220, 1190, 1170, 1140, 1085, 1035, 1010, 960, 935, 900, 855, 840, 765, 720, 680, 655.

EXAMPLE 9

1[2-(4-(4-chlorobenzoyl)-phenoxy)-2-methyl propanoyloxy]2-(2-nicotinoyloxy) ethane A solution of 3.3 g (8.6 millimoles) of 2-(2-(4-(4-chlorobenzoyl) phenoxy)-2-methyl propanoyloxy)-1-chloroethane in 15 ml of dimethylformamide was added slowly to a suspension of sodium nicotinate in 20 ml of dimethylformamide at 150°–155° C. After stirring for 3 hours at 150°–155° C., cooling to room temperature, filtering and evaporation of the filtrate, the residual was dissolved in 30 ml of ethylic ether and washed twice with 15 ml of a 8% NaHCO$_3$ aqueous solution. The ethereal phase was twice extracted by means of a 1.2 N HCl aqueous solution; the acidic phases, joined together, were washed with ethylic ether, neutralized with a NaHCO$_3$ aqueous solution and finally extracted twice with ethylic ether. The ethereal phases, joined together, were washed with water, dried and evaporated under vacuum, thus obtaining a residual which turned into dust with 4 ml of ethylic ether. 2.3 g of product (m.p. 89°–90° C.) were obtained with a yield of 56.8%.

I.R. spectrum: 3060, 2980, 2940, 1730, 1645, 1600, 1585, 1500, 1475, 1430, 1420, 1390, 1370, 1300, 1285, 1270, 1250, 1180, 1160, 1145, 1105, 1090, 1025, 980, 930, 860, 840, 770, 740, 705, 660.

EXAMPLE 10

1-[2-(4-(4-chlorobenzoyl)-phenoxy)-2-methyl-propanoyloxy]-3-nicotinoyloxy propane This product (m.p. 70°–71° C.) was obtained with a yield of 54%, starting from 3-(2-(4-(4-chlorobenzoyl)-phenoxy)-2-methyl propanoyloxy)-1-chloropropane and operating similarly to Example 8.

I.R. spectrum: 3050, 2960, 2890, 1720, 1645, 1590, 1500, 1460, 1420, 1385, 1360, 1315, 1285, 1275, 1250, 1175, 1140, 1085, 1050, 1025, 980, 955, 930, 855, 840, 765, 740, 700.

EXAMPLE 11

1-[2-(4-(4-chlorobenzoyl)-phenoxy)-2-methyl propanoyloxy]-2-(nicotinoylamino) ethane oxalate.

A solution containing 3.6 g (21.6 millimoles) of N-(2-hydroxyethyl)nicotinamide and 3.11 g of triethylamine in 30 ml of chloroform was added to a solution of 7.56 g (22.5 millimoles) of 2-(4-(4-chlorobenzoyl)-phenoxy)-2-methyl propanoy chloride in 30 ml of chloroform was added to a solution of 7.56 g (22.5 millimoles) of 2-(4-(4-chlorobenzoyl)-phenoxy)-2-methyl propanoyl chloride in 30 ml of chloroform under reflux while stirring. After stirring for 6 hours, cooling and filtering, the filtrate was washed with a HCl aqueous solution, with NaOH aqueous solutions and with water.

After drying and evaporation under vacuum, the residual was dissolved in ethylic ether and treated with oxalic acid, thus precipitating 6.6 g of product (m.p. 137°–138° C.) with a yield of 54.7%.

I.R. spectrum: 3410, 3080, 3040, 2980, 2940, 2880, 1720, 1645, 1590, 1525, 1460, 1435, 1415, 1385, 1300, 1280, 1245, 1170, 1140, 1085, 1010, 970, 930, 855, 840, 765, 700.

EXAMPLE 12

N-methyl-2.2-bis(2-(4-(4-chlorobenzoyl) phenoxy)-2-methylpropanoyloxy) diethylamine chlorydrate A solution of 5.6 g (16.6 millimoles) of 2-(4-(4-chlorobenzoyl)-phenoxy)-2-methylchloride in 30 ml of toluene was added to a solution of 1.0 g of N-methyl-diethanolamine (8.3 millimoles) and 3.5 ml of triethylamine in 20 ml of toluene. The solution was heated under reflux for 12 hours.

After cooling, filtering, washing with water, with NaOH aqueous solutions and finally again with water, drying and evaporation under vacuum, the residual was dissolved in 60 ml of ethylic ether/ethanol mixture 1:1 (v/v) and was poured into a solution of 0.747 g (8.3 millimoles) of oxalic acid in a mixture ethylic ether/ethanol. The precipitated oxalate (m.p. 116°–117° C.), was filtered, washed on the filter with ethylic ether, dissolved in 30 ml of chloroform, washed with NaOH solutions and with water. After drying, saturation with gaseous hydrogen chloride and evaporation of the solvent, 2.8 g of a viscous product which slowly crystallizes (m.p. 56°–57° C.), with a yield of 44.5%.

I.R. spectrum: 3060, 2980, 2930, 2890, 1735, 1650, 1590, 1500, 1460, 1420, 1385, 1310, 1300, 1275, 1245, 1170, 1130, 1080, 1010, 965, 955, 925, 850, 835, 760, 680.

EXAMPLE 13

N-(2-(4-(4-chlorobenzoyl)-phenoxy)-2-methyl propanoyl)-DL-2- amino-2-methylacetate of ethyl A solution of 3.36 g (10 millimoles) of 2-(4-(4-chlorobenzoyl)-phenoxy)-2-methylpropanoyl chloride in 15 mml of pyridine was added to a solution of 1.53 g (10 millimoles) of DL-alanine ethylester chlorhydrate in 30 ml of pyridine.

After stirring for 4 hours at room temperature and heating for 12 hours at 60°–70° C., the solvent was evaporated. Then 30 ml of chloroform were added. Repeated washings with aqueous NaHCO$_3$, with aqueous HCl and finally with water were carried out. After drying and evaporation of the solvent, the residual was crystallized from an ethylic ether/n-esane mixture (1:1), thus obtaining 2.58 g of product (m.p. 94°–96° C.) with a yield of 62%.

EXAMPLE 14

N-(2-(4-(4-chlorobenzoyl)-phenoxy)-2-methyl propanoyl)-DL-2- amino-2-methylacetic acid The ester obtained in Example 1 was hydrolyzed under heating with sodium hydroxide in aqueous ethanol. The product (m.p. 172°–173° C.) was crystallized from water with a yield of 97%.

EXAMPLE 15

N-(2-(4-(4-chlorobenzoyl)-phenoxy)-2-methyl propanoyl)-N-methyl-2-amino acetate of ethyl A solution of 3.36 g (10 millimoles) of 2-(4-(4-chlorobenzoyl)-phenoxy)-2-methylpropanoyl chloride in 15 ml of pyridine was added at cool to a solution of 1.53 g (10 millimoles) of N-methyl-2-amino acetate of ethyl chlorohydrate (sarcosine chlorydrate) in 30 ml of pyridine. After stirring for 4 hours at room temperature and for 12 hours at 60°–70° C., the solvent was evaporated. Then 30 ml of chloroform were added. Repeated washings with aqueous NaHCO$_3$, with aqueous HCl and finally with water were carried out. After drying and evaporation of the solvent, the residual was crystallized from ethanol at cool, thus obtaining 2.40 g of product (m.p. 90°–91° C.) with a yield of 57.7%.

EXAMPLE 16

N-(2-(4-(4-chlorobenzoyl)-phenoxy)2methyl-propanoyl)-N-methyl-2-amino acetic acid The ester obtained in Example 15 was hydrolyzed under heating in aqueous ethanol with sodium hydroxide, thus obtaining a product (m.p. 186°–187° C.) which turned into dust at cool (yield 95%).

EXAMPLE 17

N-(2-(4-(4-chlorobenzoyl)-phenoxy)-2-methyl-propanoyl)-N-amino piperidine 1.0 ml of triethylamine and 1.68 g (5 millimoles) of 2-(4-chlorobenzoyl)-phenoxy)-2-methylpropanoyl chloride in 10 ml of benzene were added to 0.50 g (5 millimoles) of N-amino piperidine in 20 ml of benzene. After 5 hours under reflux, a cooling was carried out. After filtering and repeated washings with aqueous NaHCO$_3$ and water, the residual was dried and the solvent was evaporated. The residual was crystallized from a benzene/petroleum ether mixture (1:1.5), thus obtaining 1.2 g of product (m.p. 148°–150° C.) with a yield of 60%.

EXAMPLE 18

2-(4-(4-chlorobenzoyl)-phenoxy)-2-methyl propanoyl oxyacetate of ethyl 1.8 ml of triethylamine were added to 1.04 g (10 millimoles) of ethyl glycolate in 20 ml of benzene. The solution was heated up to reflux and slowly 3.36 g (10 millimoles) of 2-(4-(4-chlorobenzoyl)-phenoxy)-2-methyl-propanoyl chloride in 15 ml of benzene were added. After 18 hours under reflux, a cooling was carried out. Then, after filtering and after repeated washings with aqueous NaHCO$_3$ and with water, the product was purified by preparative chromatography, using a column of silica gel and chloroform/methanol mixture (97.5:2.5)(Rf=0.90) as eluent.

The separated whitish oil solidified after a few days and was crystallized from n-esane, thus obtaining 2.05 g of product (m.p. 70°–72° C.) with a yield of 50.7%.

EXAMPLE 19

N-(2-(4-(4-chlorobenzoyl)-phenoxy)-2-methyl propanoyl)-L-2-amino-2-p-hydroxyphenylacetate of ethyl 15 ml of triethylamine and 3.36 g (10 millimoles) of 2-(4-(4-chlorobenzoyl)-phenoxy)-2-methyl propanoyl chloride in 20 ml of chloroform were added, slowly at room temperature, to 1.95 g (10 millimoles) of 2-amino-2-p-hydroxyphenylacetate of ethyl (L-tirosine ethylester) in 40 ml of chloroform. After stirring for 48 hours at room temperature, repeated washings were carried out with aqueous NaHCO$_3$, with aqueous HCl and with water.

The residual oil was dried, evaporated under vacuum and crystallized from a mixture n-butyl-bromide/petroleum ether (2:1), thus obtaining 3.55 g of product (m.p. 99°–102° C.) with a yield of 71%.

EXAMPLE 20

N-(2-(4-(p-chlorobenzoyl)-phenoxy)-2-methyl propanoyl)-L-2-amino-2-p-hydroxyphenylacetic acid The ester obtained in Example 19 was hydrolyzed under heating with sodium hydroxide in aqueous methanol. The product was obtained as an oil which solidified slowly giving a hygroscopic solid (m.p. 101°–103° C.) with a yield of 68%.

EXAMPLE 21

N-(2-(4-(4-chlorobenzoyl)-phenoxy)-2-methyl propanoyl)-DL-2-amino-2-benzylacetate of ethyl 8 ml of triethylamine were added to 4.30 g (20 millimoles) of DL-2-amino-2-benzylacetate of methyl chlorydrate (DL-phenylamine methylester chlorydrate) in 50 ml of CHCl$_3$. Slowly at room temperature, 6.72 g (20 millimoles) of 2-(4- (4-chlorobenzoyl)-phenoxy)-2-methyl propanoyl chloride were added. After stirring for 2 hours at room temperature and for 7 hours under reflux, repeated washings with aqueous NaHCO$_3$, with aqueous HCl and with water were carried out. After drying and evaporation under vacuum, the residual oil was crystallized from a chloroform/n-esane mixture (1:7.5), thus obtaining 6.4 g of product (m.p. 89°–91° C.) with a yield of 67%.

EXAMPLE 22

N-(2-(4-(4-chlorobenzoyl)-phenoxy)-2-methyl propanoyl)-DL-2- amino-2-benzylacetic acid The ester obtained in Example 21 was hydrolyzed under heating with sodium hydroxide in aqueous ethanol and the product was crystallized from a benzene/petroleum ether mixture (1:0.5), thus obtaining 1.8 g of product (m.p. 169°–170° C.) with a yield of 75%.

EXAMPLE 23

N-(2-(4-(4-chlorobenzoyl)-phenoxy)-2-methyl propanoyl)-L-2-amino-2-hydroxymethyl acetate of methyl 3.5 ml of triethylamine and 1.68 g (5 millimoles) of 2-(4-(4-chlorobenzoyl)-phenoxy)-2-methyl propanoyl chloride in 15 ml of chloroform were added, slowly at room temperature, to 0.78 g (5 millimoles) of L-2-amino-2-hydroxymethyl acetate of methyl chlorhydrate (L-serine methylester chlorydrate) in 30 ml of chloroform. After stirring for 48 hours, repeated washings with aqueous NaHCO$_3$, with water and finally with aqueous HCl were carried out. After drying and evaporation under vacuum, an oil was obtained, which did not crystallize and was purified by thin layer chromatography, using a mixture benzene/dioxane.acetic acid (90:10:12) as eluent (Rf=0.48), thus obtaining 1.4 g of product with a yield of 67%.

EXAMPLE 24

N-(2-(4-(4-chlorobenzoyl)-phenoxy)-2-methyl propanoyl)-L-2-amino-2-hydroxymethyl acetic acid The ester obtained in Example 23 was hydrolyzed under heating with sodium hydroxide in aqueous methanol and the product was crystallized from a ethanol-/ethylic ether mixture (1:3.5) and finally from benzene, thus obtaining the product (m.p. 84°–86° C.) with a yield of 87%.

EXAMPLE 25

2-(4-(4-chlorobenzoyl)-phenoxy)-2-hydroxymethyl propanoate of ethyl

0.21 g (9 millimoles) of methanol sodium in 15 ml of ethanol were added slowly at room temperature to 1.98 g (9 millimoles) of 4-(4-chlorobenzoyl)-phenol in 10 ml of ethanol. After 1 hour at 50° C., 2.1 g (9 millimoles) of 2-hydroxymethyl-2-bromine-propanoate of ethyl (according to L. Eoetvoes, Acta Chim. Acad. Sci. Hung. 49 (3) 287-90 -1966) in 5 ml ethanol were added slowly. After 26 hours under reflux, an evaporation under vacuum was carried out. Then ethylic ether and sodium hydroxide were added. The ethereal phase was repeatedly washed with sodium hydroxide and finally with water. After drying and evaporation, 3.1 g of product (m.p. 93°-95° C.), which partially crystallized from n-esane, were obtained with a yield of 40%.

EXAMPLE 26

3-N-(2-(4-(4-chlorobenzoyl)-phenoxy)-2-methyl-propanoyl)-amino-1-nicotinoyl oxy-propane

3.4 ml of triethylamine and 1.416 g (8 millimoles) of nicotinoyl chloride chlorhydrate were added, slowly at 50° C., to 3.0 g (8 millimoles) of 3-N-(2-(4-(4-chlorobenzoyl)-phenoxy)-2-methyl propanoyl)-amino-propane-1-ol in 40 ml of benzene.

The 3-N-(2-(4-(4-chlorobenzoyl)-phenoxy)-2-methyl propanoyl)-amino-propane-1-ol had been prepared by condensation of 2-(4-(4-chlorobenzoyl)-phenoxy)-2-methylpropanoylchloride with 1-amino-3-hydroxy-propane (m.p. 92°-93° C.).

After 24 hours under reflux, a filtration and some washings with aqueous NaHCO$_3$ and water were carried out. After drying and evaporation under vacuum, the residual oil was crystallized from a benzene/petroleum ether mixture (20:15), thus obtaining 1.8 g of product (m.p. 94°-95° C.) with a yield of 47%.

EXAMPLE 27

Bis-(2-(4-(4-chlorobenzoyl)-phenoxy)-2-methyl propanoyl) thiodiethylenglycol

1.6 ml of triethylamine and slowly 3.36 g (10 millimoles) of 2-(4-(4-chlorobenzoyl)-phenoxy)-2-methyl propanoyl chloride in 15 ml of benzene were added to 0.61 g (5 millimoles) of thiodiethylenglycol in 50 ml of benzene. After 24 hours under reflux, a filtration and repeated washings with aqueous NaHCO$_3$ and water were carried out. By drying and evaporation, an oil was obtained which was purified by chromatography, using a column of silica gel and a chloroform/methanol mixture (97.5::2.5) (Rf=0.95), thus obtaining 2.1 g of product with a yeild of 61%.

EXAMPLE 28

2-(4-(4-chlorobenzoyl)-phenoxy)-2-hydroxymethyl propionic acid

The ester prepared according to Example 25 was hydrolyzed under heating with sodium hydroxide in aqueous ethanol and the product was crystallized from toluene, thus obtaining the product (m.p. 172°-174° C.) with a yield of 95.8%.

EXAMPLES 1 TO 28

Evaluation of normolipaemizing activity on hypertriglyceridaemia by fructose

Male Wistar rats, weighted 240±10 g, normally fed, subdivided in groups of 6 animals each, were used.

The products to be evaluated were administered through oral way at the dose of 0.2 millimole/Kg, either in an arabic gum suspension at 5% or in an aqueous solution having a volume of 1 ml per 100 g of animal.

A first group of animals (for the control) were treated with the solvent used to bring the products into solution or suspension.

A second group of animals received a solution at 20% of fructose as drinking water and were treated with the solvent.

A third group of animals received a solution at 20% of fructose as drinking water and were treated with the products of this invention and, for the prupose of comparison, with 2-(4-(4-chlorobenzoyl)-phenoxy)methylpropionic acid isopropyl ester (indicated as Procetofene ester) and with 2-(4-(4-chlorobenzoyl)-phenoxy)methylpropionic acid (indicated as Procetofene acid).

On the third day, the triglycerides determination was carried out according to the method of M. Eggstein, F. H. Krentz (Klin. Wschr. 44, 262; 1966) and F. H. Schmidt, K. Von Dahl (Z. Klin. Chem. 6, 156; 1968) was carried out on the blood withdrawn from the heart of the animal.

The results, indicated as the decrease percent of triglycerides content in the blood of the animals treated with the product under evaluation with respect to tryglycerides content in the blood of the animals treated only with fructose, are shown in the following table.

| Product | Triglycerides decrease % |
|---|---|
| Example 1 | 50.7 |
| Example 3 | 58.4 |
| Example 4 | 56.2 |
| Example 6 | 46.3 |
| Example 7 | 54.0 |
| Example 8 | 50.0 |
| Example 9 | 35.5 |
| Example 10 | 54.9 |
| Example 11 | 56.7 |
| Example 12 | 53.1 |
| Example 13 | 51.0 |
| Example 14 | 44.0 |
| Example 15 | 41.0 |
| Example 16 | 45.0 |
| Example 17 | 71.0 |
| Example 18 | 34.0 |
| Example 19 | 40.0 |
| Example 20 | 52.0 |
| Example 21 | 55.0 |
| Example 22 | 52.0 |
| Example 23 | 67.0 |
| Example 24 | 66.0 |
| Example 25 | 48.0 |
| Example 26 | 77.0 |
| Example 27 | 40.0 |
| Example 28 | 58.0 |
| Procetofene ester | 48.5 |
| Procetofene acid | 51.8 |

We claim:
1. A compound of the formula:

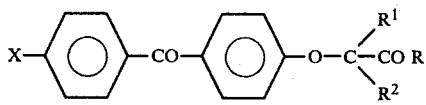

wherein:
X represents an atom of chlorine, bromine, iodine or an alkyl group having 1 to 4 carbon atoms;
R¹ and R², equal or different from each other, represent a hydrogen atom or an alkyl group or a hydroxyalkyl group, said groups having 1 to 6 carbon atoms;
R represents a group selected from:

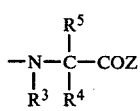

wherein:
R³ represents a hydrogen atom or an alkyl group, R⁴ and R⁵, equal or different from each other, represent a hydrogen atom or an alkyl, an hydroxyalkyl, mercaptoalkyl, alkylaryl, or phenyl group, wherein the alkyl groups have up to 6 carbon atoms and each phenyl group may have an OH substituent and
Z represents an OH,
NH—CH₂CONH—CH₂COOH or
—O—CH₂—COOH or a pharmaceutically acceptable salt of said compound.

2. The compound of claim 1 wherein its acid group is salified with a non-toxic cation.
3. The compound of claim 1 wherein it contains a basic group salified with a non-toxic anion.
4. A pharmaceutical preparation useful in the therapy of hyperlipaemia and of hypercholesterolemia, characterized in that it contains a hypolipaemic or hypocholesterolmeic effective dose of at least one of the compounds of claim 5 associated or combined with one or more usual excipients or solvents.
5. The compound of claim 1 which is (2-(4-(4-chlorobenzoyl)phenoxy)-2-methyl propanoyl) aminoacetic acid.
6. The compound of claim 1 which is (2-(4-(4-chlorobenzoyl)-phenoxy)-2-methyl propanoyl)amino acetyl amino acetic acid.
7. The compound of claim 1 which is N-(2-(4-(4-chlorobenzoyl)-phenoxy)-2-methyl propanoyl)-DL-2-amino-2-methylacetic acid.
8. The compound of claim 1 which is N-(2-(4-(4-chlorobenzoyl)-phenoxy)-2-methyl propanoyl)-N-methyl-2-amino acetic acid.
9. The compound of claim 1 which is N-(2-(4-(4-chlorobenzoyl)-phenoxy)-2-methyl propanoyl)-L-2-amino-2-p-hydroxyphenylmethyl acetic acid.
10. The compound of claim 1 which is N-(2-(4-(4-chlorobenzoyl)-phenoxy)-2-methyl propanoyl)-L-2-amino-2-hydroxymethyl acetic acid.
11. The compound of claim 1 which is 2-(4-(4-chlorobenzoyl)-phenoxy)-2-hydroxymethyl propionic acid.
12. The compound of claim 1 which is N-(2-(4-(4-chlorobenzoyl)-phenoxy)-2-methyl propanoyl)-DL-2-amino-2-benzylacetic acid.

* * * * *